(12) United States Patent
Weinstein et al.

(10) Patent No.: US 7,156,089 B2
(45) Date of Patent: Jan. 2, 2007

(54) METHOD AND DEVICE FOR TREATMENT OF RESPIRATORY TRACT DISORDERS

(76) Inventors: Robert E. Weinstein, 177 Commonwealth Ave., Boston, MA (US) 02116; Allan M. Weinstein, 9205 Pegasus Ct., Potomac, MD (US) 20854

( * ) Notice: Subject to any disclaimer, the term of this patent is extended or adjusted under 35 U.S.C. 154(b) by 335 days.

(21) Appl. No.: 10/461,198

(22) Filed: Jun. 11, 2003

(65) Prior Publication Data

US 2003/0234198 A1 Dec. 25, 2003

Related U.S. Application Data

(60) Provisional application No. 60/389,945, filed on Jun. 19, 2002.

(51) Int. Cl.
*A61M 11/00* (2006.01)
*A61L 9/04* (2006.01)
*B65D 85/42* (2006.01)

(52) U.S. Cl. .................... 128/200.19; 128/200.23; 424/405; 206/538

(58) Field of Classification Search ........... 128/200.23, 128/200.14, 203.14, 203.12, 200.19, 205.21, 128/205.23; 206/534, 538, 828, 528, 530, 206/529, 532, 562, 563, 564; 424/489, 45, 424/400, 451, 464
See application file for complete search history.

(56) References Cited

U.S. PATENT DOCUMENTS

| | | | |
|---|---|---|---|
| 4,039,080 A | 8/1977 | Cappuccilli | |
| 4,553,670 A | 11/1985 | Collens | |
| 4,593,819 A | 6/1986 | Will | |
| 4,736,849 A | 4/1988 | Leonard et al. | |
| 5,181,189 A | 1/1993 | Hafner | |
| 5,377,841 A | 1/1995 | Varon | |
| 5,482,030 A * | 1/1996 | Klein | 128/200.23 |
| 5,489,026 A | 2/1996 | D'Aloia | |
| 5,489,027 A | 2/1996 | Goerigk | |
| 5,830,490 A | 11/1998 | Weinstein et al. | |
| 5,941,241 A | 8/1999 | Weinstein et al. | |
| 6,187,291 B1 * | 2/2001 | Weinstein et al. | 424/45 |
| 6,382,205 B1 | 5/2002 | Weinstein et al. | |
| 6,571,790 B1 * | 6/2003 | Weinstein | 128/200.19 |
| 6,792,939 B1 * | 9/2004 | Weinstein | 128/200.19 |
| 6,843,372 B1 * | 1/2005 | Weinstein | 206/534 |

* cited by examiner

*Primary Examiner*—Henry Bennett
*Assistant Examiner*—Shumaya B. Ali
(74) *Attorney, Agent, or Firm*—Robert R. Deleault, Esq.; Mesmer & Deleault, PLLC (57) ABSTRACT

An organizational treatment device and method for the treatment of obstructive pulmonary disease comprising both controller and rescue medications such that the need for rescue medication and consequent need for controller medication can be more certainly determined than at present.

25 Claims, 4 Drawing Sheets

METHOD AND DEVICE FOR TREATMENT OF RESPIRATORY TRACT DISORDERS

This application claims the benefit of U.S. Provisional Application No. 60/389,945 filed Jun. 19, 2002.

BACKGROUND OF THE INVENTION

1. Field of the Invention

The present invention relates generally to devices and methods of treating respiratory tract disorders. Particularly, the present invention relates to the treatment of obstructive pulmonary disease. More particularly, the present invention relates to the treatment of obstructive pulmonary disease with topical controller medications and topical rescue medications as a regimen where the dosage of one medication is a determinant for the need for the other medication in a particular individual.

2. Description of the Prior Art

Obstructive lung diseases are diseases that are characterized by narrowing and inflammation of the bronchial air flow tract. Asthma is an example of an obstructive respiratory tract disorder. Symptoms consist of coughing, excessive sputum productions, wheezing, and shortness of breath. Symptoms typically vary in severity over time and, of the obstructive respiratory disorders, changes in severity are most prominent and rapidly occurring with asthma.

Obstructive lung diseases are generally chronic and require long-term treatment. One approach to treatment is directed at preventing symptoms. Medications used for this purpose are referred to as "preventative" or "controller" therapy. In the event that symptoms flare despite the use of controller therapy, it becomes necessary to utilize medication to bring about immediate relief. Medications used for this purpose are often referred to as "rescue" medications.

Adrenergic agonists are commonly used to reverse bronchial tree spasm occurring with obstructive pulmonary disorders. Both long-acting and short-acting forms are available. Long-acting forms are often employed when such agents are used to prevent symptoms. An example of a long-acting agent is the selective beta2-adrenergic bronchodilator known as salmeterol xinafoate and marketed under the trademark Serevent®. It is used both as an inhaled dry powder aerosol and as an aerosolizable liquid in a metered dose inhaler.

In the event of a breakthrough of symptoms, it is preferable not to use additional doses of long-acting adrenergic agents for concern of accumulation of medication. Adrenergic agents have adrenalin-like effects such as nervousness and rapid heart beat. Accumulation or overdose of such medication can have potentially dangerous consequences such as irregularities of the heart rhythm. An adrenergic agent with an immediate effect and short duration of action is therefore preferred for relief of acute symptomatic breakthrough. An example of such an adrenergic agent is albuterol USP, which is an aerosolizable liquid in a metered dose inhaler marketed under the trademark Ventolin®.

Corticosteroids are another type of medication that can be used as controller medication. Corticosteroids do not have immediate effects on symptoms, but rather reduce inflammation over a longer term. Examples of aerosolized forms of such agents are fluticasone propionate that is marketed as an inhaled powder aerosol under the trademark Flovent®, and beclomethasone dipropionate USP, which is marketed under the trademark Beclovent®, an MDI. The administration of such medications by aerosol allows them to be directed topically to the site of inflammation within the bronchial tree and has the advantage of minimizing systemic effects that are more likely to occur with oral or other systemic administration. Even administered topically, however, some systemic absorption (hypercorticism) and adrenal suppression may occur, particularly at higher doses. Because these medications are often required over long periods, they pose cumulative risks. In children, growth suppression is of particular concern and, in adults, reduction in bone density is a problem. Such agents are best employed judiciously for therapeutic benefit while avoiding overuse and side-effects.

Many drugs are utilized by patients over a period of time in varying amounts and in varying order to provide for their effective administration. Packaging has been developed for aiding the user of such drugs to comply with the proper administration over the proper time period. The dispensing apparatus associated with such multiple-day administrative drugs are typically directed to the administration of pills or capsules, or similar solid medication.

U.S. Pat. No. 4,039,080, for example, discloses a tray having individual compartments for pills that may contain a week's medication with indicia indicating the day of the week and time of the day the medication is to be taken.

U.S. Pat. No. 4,553,670 discloses another device comprising a support on which are located two different ingestible medicinal substances in a single dose form with an adjacent portion for instructional information.

U.S. Pat. No. 4,593,819 discloses a covered pill tray of rectangular configuration having an array of open-topped compartments to hold a supply of medication arranged by the day and time of taking the medication.

U.S. Pat. No. 4,736,849 discloses a method and another type of dispenser for the storage and dispensing of calendar-oriented pills.

U.S. Pat. No. 5,181,189 discloses a device for storage and time-regulated dispensing of drugs which includes a drug container to which is secured a signal generator.

U.S. Pat. No. 5,377,841 discloses a sleep therapy package which includes an audio recording of program material for inducing sleep, a card having a plurality of doses, some of which are medicine for inducing sleep and at least one of which is a placebo, along with patient instructions.

Cartonless packaging systems for containing liquids used, for example, as ophthalmic products, which also contain means for storing tablets and instructional material are disclosed in U.S. Pat. Nos. 5,489,026 and 5,489,027.

U.S. Pat. No. 5,830,490 discloses a device and method for a lay person to organize topical medications together with oral medications.

U.S. Pat. Nos. 5,941,241 and 6,382,205 disclose a device and method for a lay person to organize combined topical medication regimens.

What is not specifically described in the aforementioned inventions is the provision of topical controller medications and topical rescue medications for the treatment of obstructive pulmonary diseases and their instruction as a regimen where the dosage of one medication is a determinant for the need for the other medication in a particular individual. Controller and rescue medications for obstructive lung disorders are presently provided separately to patients. This introduces the potential for users: (a) not having one or the other medication due to its not being prescribed or being overlooked, (b) overusing one of the agents if the other is unavailable, (c) being confused in identifying the agents, and/or (d) being unsure of how to coordinate the medications together. This also introduces the potential for caregiver confusion in assessing the relative use of the individually prescribed and filled medications or even knowing with certainty if one is being filled by the patient and not the other.

Therefore, what is needed is treatment kit that reduces the likelihood of having only one of the controller or rescue medications. What is also needed is a treatment kit that reduces the likelihood of overuse of one of the medications by the patient. What is further needed is a treatment kit that reduces the likelihood of a patient confusing one medication for the other. What is still further needed is a treatment kit that reduces the likelihood of confusion over the coordination of treatment medications together as a regimen.

SUMMARY OF THE INVENTION

It is an object of the present invention to provide a treatment kit for treating an obstructive respiratory tract disorder that reduces the likelihood of a patient having only one of the controller or rescue medications. It is another object of the present invention to provide a treatment kit that reduces the likelihood of a patient overusing one of the medications. It is still another object of the present invention to provide a treatment kit that reduces the likelihood of a patient confusing the controller medication with the rescue medication. It is still another object of the present invention to provide a treatment kit that reduces the likelihood of patient confusion of the proper coordination of the controller and rescue agents as a regimen of interdependent medications. It is a further object of the present invention to increase the certainty of caregivers knowing that the patient has been provided with both controller and rescue agents. It is yet another object of the present invention to enhance the caregiver's ease of determining the use of rescue agent relative to controller agent, such information being useful for adjusting controller agent dosing.

The present invention achieves these and other objectives by providing a unifying dispensing container for therapeutic agents for the treatment of respiratory disorders, which incorporates both controller and rescue medications. The unifying container additionally includes indicia for distinguishing these controller and rescue agents and instructions for their use together as a therapeutic regimen. Two essential aspects of the instructions of the present invention are to direct the user to use rescue medication for breakthrough symptoms and also to alert the user to over-utilization and/or over-reliance upon rescue medication. The inclusion of both controller and rescue medication in the prepackaged, unified dispensing container of the present invention results in certainty that the user has both medications when the package is procured.

The severity of symptoms of bronchospastic disease such as asthma is known to vary between affected individuals and also to vary with time in a single individual. Caregivers are therefore required to estimate treatments in accord with the general severity of symptoms and also variability of symptoms in a particular individual, and to attempt to prescribe the optimal amount of controller medication for prevention, neither more nor less than what is needed. One parameter for making this assessment is need for rescue medication. When controller and rescue medications are separately purchased, it becomes difficult for a caregiver to keep track of rescue medication use. This would be improved if both were obligatorily purchased at the same time. In this case, the inclusion of both controller and rescue medications in a single package would serve as a yardstick for medication utilization and need. As a convention, controller medications such as Advair® and Severent® are presently packaged in inhalers that provide actuations sufficient for one month of use. The common rescue medication, Ventolin Inhalation Aerosol® is packaged in canisters that contain either 80 or 200 actuations. If both controller and rescue medications were supplied once per month in the single prepackaged format of the present invention, a caregiver would have a starting point each month for estimating rescue-to-controller medication use and therefore preventing rescue overuse and anticipating controller medication need. Furthermore, simple examination of the medication canisters or remaining tablets of the package would also allow an estimation of relative use.

In a preferred embodiment, the present invention would also incorporate a device to monitor the use of the rescue medication. The rescue medication actuation monitor or counter would provide a numerically objective parameter that could be used to adjust the selection and dosing of controller medication. An example of a device to keep track of aerosol actuations is available under the trademark THE DOSER™ manufactured by MEDITRACK Products of Hudson, Mass. It is to be understood that the actuation monitor/counter may be separate from the rescue medication aerosol delivery device and adapted to be used with it, or may be an integral part of the rescue medication inhaler device. Further, it is to be understood that controller medication may be given in topical, aerosolized form or oral systemic form, and that rescue medication is delivered topically to the bronchial tree by aerosolization. The word "aerosolization" encompasses its ordinary dictionary meaning of providing a suspension of fine solid or liquid particles in air or gas. Likewise, the word "regimen" is intended to convey its ordinary dictionary meaning of a regulated system or procedure intended to maintain health. For the present invention, the regimen is an ongoing course of treatment that incorporates both interdependent controller and rescue medicines where the dosage of one medication is a determinant of the need for the other medication in a particular individual.

Treatments which necessitate a multiplicity of components pose a number of problems for patients. Such multiple medication treatments may be a source of confusion and frustration which can result in medication error or lack of compliance. The multiplicity of components may lack coordinating indicia and instructions for verifying the multiple component use together. Patients may lose track of which medication is which. Individual components may be lost, misplaced, or ignored, particularly so with instructions issued separately from the medication. Furthermore, in spite of careful oral and written instruction from the health care provider, many patients are known to use what they have conveniently available. Haphazard applications, in the case of obstructive lung disease, can not only result in poor symptom control, but overuse of controller medication and undesirable side effects can be the result of failure to optimize treatment. The devices and methods of the present invention would help overcome these noted problems.

The device of the present invention allows a caregiver greater certainty as to the patient's use of rescue medication in relation to controller medication, and at least the knowledge that the patient is not using rescue medication in excess of controller medication in that they are concomitantly dispensed. Frequent need for the user to resort to rescue medication would indicate the need for a greater dosage of controller medication. Conversely, negligible need for rescue medication serves as a signal that controller medication dosage might be lowered. It is of particular importance to avoid unnecessary long-term side effects of corticosteroids.

The packaging together of controller and rescue medications according to the present invention would provide a point of departure for a user to assess rescue medication use and is an improvement over these medications being separately procured. Both the current rescue medication and current controller medication of the package could then be inspected by either caregiver or patient to roughly gauge unused medication and use of rescue medication relative to controller medication. The addition of a rescue medication actuation counter, if desired, would provide a yet more precise record of rescue inhalations.

DETAILED DESCRIPTION OF THE PREFERRED EMBODIMENT

Figure 1:
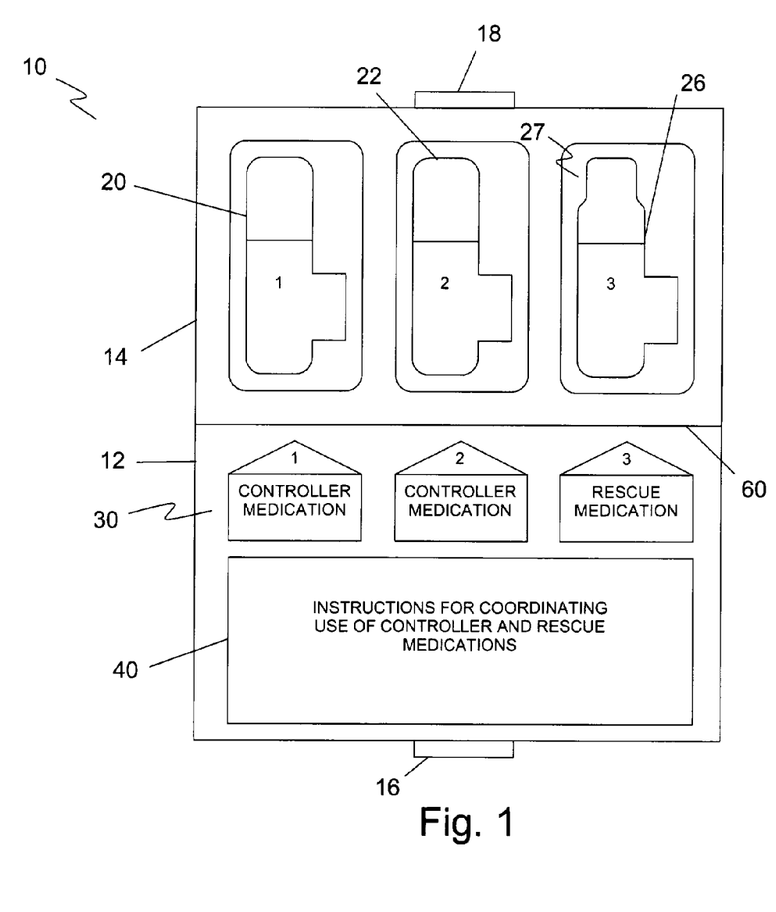
FIG. 1 is a plan view of one embodiment in accordance with the present invention.

The preferred embodiment(s) of the present invention are illustrated in FIGS. 1–4. FIG. 1 illustrates a support package 10 that houses first and second topical controller medications 20, 22 in multi-dosage aerosol units and a topical rescue medication 26 also in multi-dosage aerosol units. Identifying indicia 30 is included with each respective medication. An instruction bearing portion 40 provides instructions for use of the controller medications 20, 22 and rescue medication 26 as a regimen.

Support package 10 includes a bottom portion 12 and a top portion 14. Bottom portion 12 has a clasp portion 16, and top portion 14 has a clasp portion 18. Clasp portion 16 and clasp portion 18 can be secured together when package 10 is folded along fold 60.

An example of such a treatment kit that may be suitable for an adult with moderately severe asthma is exemplified by Example 1, which contains two individual topical controller medications and a topical rescue medication where first controller medication 20 is Controller Medication #1 and second controller medication 22 is Controller Medication #2.

EXAMPLE 1

| Controller Medication #1 | Controller Medication #2 | Rescue Medication |
|---|---|---|
| Serevent ® Inhalation Aerosol 2 sprays twice-daily (each actuation delivering 25 mcg of salmeterol base) | Flovent ® 110 mcg Inhalation Aerosol 2 sprays twice-daily | Ventolin ® Inhalation Aerosol 2 sprays every 4–6 hours not to exceed 8 sprays per 24 hours (each actuation delivering 100 mcg albuterol, USP) |

The controller medication #1 is Serevent® (salmeterol xinafoate) Inhalation Aerosol which is indicated for long-term maintenance of bronchodilitation in patients 12 years of age and older. The usual dosage is two inhalations twice daily, morning and evening at approximately 12 hour intervals. Its FDA approved dosing recommendation states that "adverse effects are more likely to occur with higher doses and more frequent administration or administration of a larger number of inhalations is not recommended." The controller medication #2 contains a corticosteroid, fluticasone propionate, and is provided by the manufacturer in 44 mcg, 110 mcg and 220 mcg strengths under the trademark Flovent®. The rescue medication contains albuterol USP and is available under the trademark Ventolin®. The present invention provides a method for helping to select the concentration and to optimize dosing of the controller medication #2. Infrequent need for the rescue medication 26 would provide an objective parameter for lowering controller medication by reducing the number of controller medication #2 inhalations and/or concentration. Conversely, frequent rescue medication use indicates continued and increased need for controller medication #2 either by increased inhalations and/or strength to control symptoms. FIG. 1 is in schematic conformation with this regimen.

Figure 2:
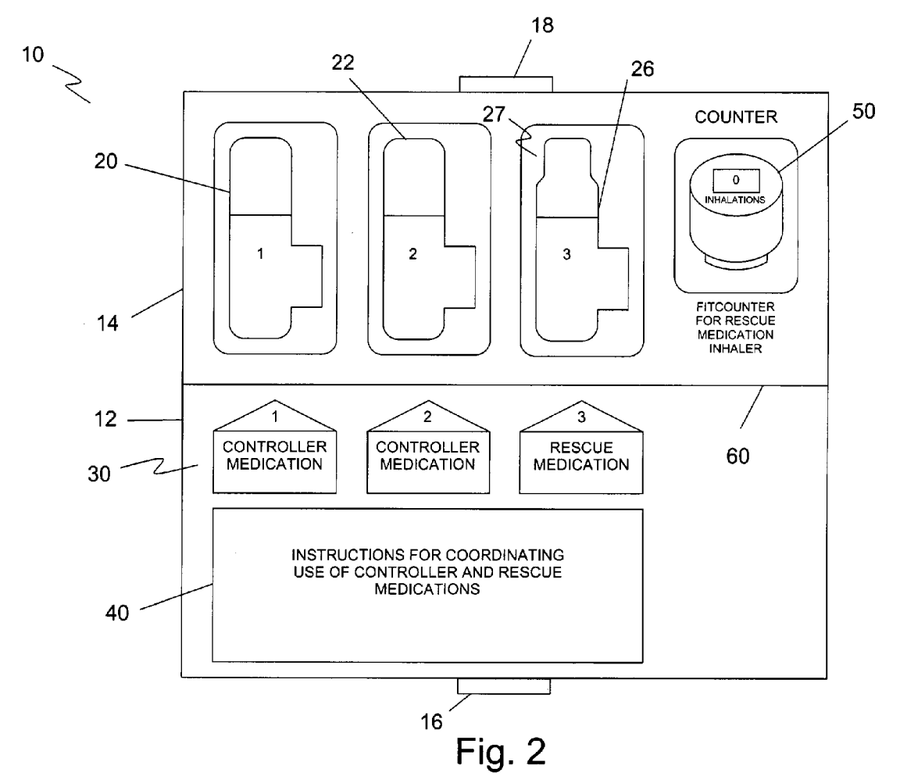
FIG. 2 is a plan view of another embodiment in accordance with the present invention.

Turning now to FIG. 2, there is illustrated another embodiment of the present invention. FIG. 2 illustrates a support package 10 that houses first and second topical controller medications 20, 22 in multi-dosage aerosol units and a topical rescue medication 26 also in multi-dosage aerosol units. Identifying indicia 30 is provided aligned with each respective medication. An instruction bearing portion 40 provides instructions for use of the controller medications 20, 22 and rescue medication 26 as a regimen. An actuation counter 50 is provided that can be placed on a counter receiving portion 27 of rescue medication 26.

Support package 10 includes a bottom portion 12 and a top portion 14. Bottom portion 12 has a clasp portion 16, and top portion 14 has a clasp portion 18. Clasp portion 16 and clasp portion 18 can be secured together when package 10 is folded along fold 60.

The medication regimens of FIG. 2 are the same as those provided in FIG. 1.

Figure 3:
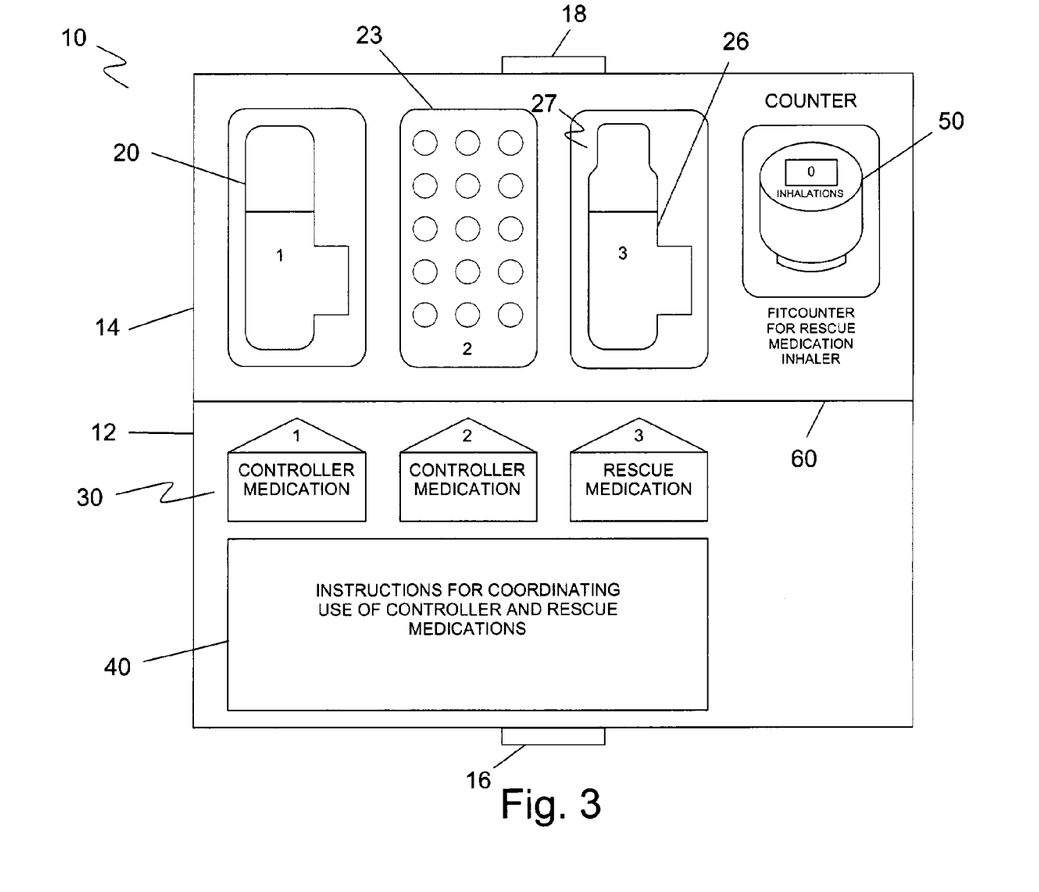
FIG. 3 is a plan view of another embodiment in accordance with the present invention.

Turning now to FIG. 3, there is illustrated another embodiment of the present invention. This embodiment also includes a support package 10 having a bottom portion 12 and a top portion 14 with clasp portions 16, 18, respectively. Support package 10 houses a first topical controller medication 20 in a multi-dosage aerosol unit, a second oral controller medication 23 for systemic dosing, and a topical rescue medication 26 also in multi-dosage aerosol units. Oral controller medication is depicted in the form of tablets on a blistered card. However, other oral dosage forms such as capsules, caplets, liquids, and other containers such as bottles as are known in the art may be used in the present invention. Identifying indicia 30 is illustrated aligned with each respective medication. Indicia to distinguish each medication within the unifying container of the present invention might alternatively or additionally be on the surface of the inhalers, blister cards, or bottles of the medications themselves, or other printed surface within the container rather than on the surface of the unifying container as illustrated. An instruction bearing portion 40 provides instructions for use of the controller medications 20, 23 and rescue medication 26 as a treatment regime. An actuation counter 50 is provided that can be placed on a counter receiving portion 27 of rescue medication 26.

The following Example 2 includes one topical controller medication 20, one oral controller medication 23 and a topical rescue medication 26.

EXAMPLE 2

| Controller Medication #1 | Controller Medication #2 | Rescue Medication |
|---|---|---|
| Flovent ® 44 mcg Inhalation Aerosol | Singulair ® Tablets (10 mg montelukast sodium) | Ventolin ® Inhalation Aerosol |
| 2 sprays twice-daily | 1 tablet at bedtime | 2 sprays every 4–6 hours not to exceed 8 sprays per 24 hours (each actuation delivering 100 mcg albuterol, USP) |

The regimen in Example 2 differs from the regimen in Example 1 by employing an oral controller medication 23, which is montelukast sodium and available under the trademark Singulair®, and exemplifying a lower dose of the inhaled corticosteroid controller medication 20 available under the trademark Flovent®. Singulair® is a selective leukotriene receptor antagonist and represents a unique class of controller medication that may allow for lower dosing and use of corticosteroid medications. The approved dosage for Singulair® montelukast sodium for the prophylaxis and chronic treatment of asthma is a fixed dosage of 10 mg in adolescents and adults 15 years of age and older, 5 mg for ages 6 to 14, and 4 mg for ages 2 to 5. This fixed dose is recommended once a day in the evening. As stated in Example 2, the need for Ventolin®, the rescue medication 26, can be assessed according to the actuation counter 50 provides an objective parameter for dosing of the controller medication Flovent®. FIG. 3 is in schematic conformation with this regimen.

Figure 4:
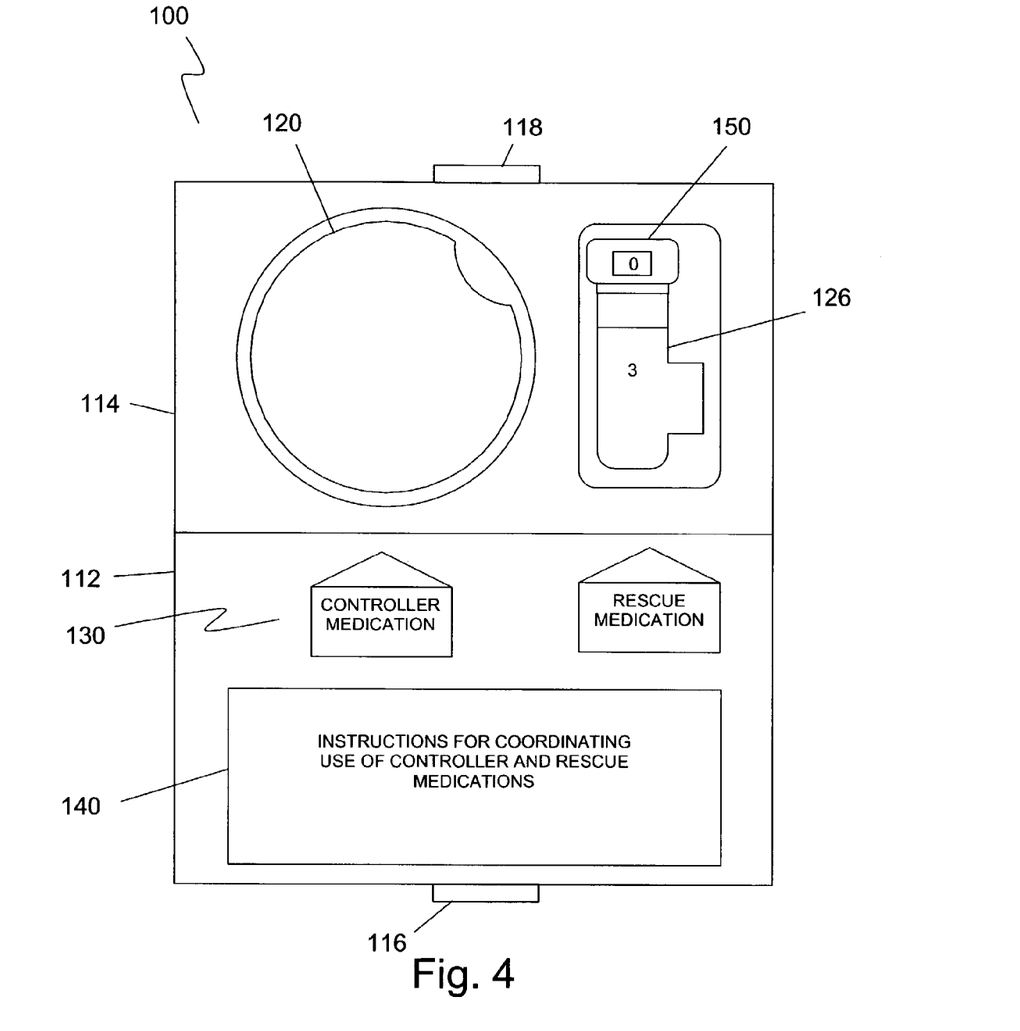
FIG. 4 is a plan view of another embodiment in accordance with the present invention.

FIG. 4 illustrates yet another embodiment of the present invention. This embodiment includes a support package 100 having a bottom portion 112 and a top portion 114 with clasp portions 116, 118, respectively. Support package 100 houses a first topical controller medication 120 in a multi-dosage, dry powder aerosol unit and a topical rescue medication 126 in a multi-dosage, liquid medication aerosol unit that incorporates an actuation counting monitor 150. Identifying indicia 130 is provided aligned with each respective medication. An instruction bearing portion 140 provides instructions for use of the controller medication 120 and rescue medication 126 as a treatment regime.

The following Example 3 includes one topical controller medication 120 and a topical rescue medication 126.

EXAMPLE 3

| Controller Medication | Rescue Medication |
|---|---|
| Advair ™ Discus ® 250/50 | Ventolin ® Inhalation Aerosol |
| 1 inhalation twice-daily | 2 sprays every 4–6 hours not to exceed 8 sprays per 24 hours (each actuation delivering 100 mcg albuterol, USP) |

The regimen in Example 3 differs from the regimen in Example 1 by employing a single controller medication 120 containing a beta-adrenergic agent and a corticosteroid in fixed relationship. Controller medication 120 is available under the trademark Advair Diskus® 250/50 and is delivered as an aerosolized powder, each inhalation containing fluticasone propionate (250 mcg) and salmeterol xinafoate (50 mcg). Advair Diskus® is recommended for regular one inhalation, twice-a-day dosing. Adjustment in dose can be made by selecting from three available strengths of Advair™ containing 100, 250 and 500 mcg of fluticasone per inhalation. All contain the same dosage of salmeterol xinafoate, which if given at higher dose is known to have a risk of adrenergic stimulatory side effects. The actuation counter 150 on rescue medication 126 records the number of times the user employs the rescue medication, Ventolin®. Actuation counter 150 provides an objective parameter for selection of the appropriate strength of Advair™. FIG. 4 is in schematic conformation with the regimen of Example 3.

Although the preferred embodiments of the present invention have been described herein, the above descriptions are merely illustrative. Further modification of the invention herein disclosed will occur to those skilled in the respective arts and all such modifications are deemed to be within the scope of the invention as defined by the appended claims.

What is claimed is:

1. A prepackaged therapeutic system that facilitates the assessment of need for controller medication in obstructive pulmonary disease, said system comprising:
    multiple dosages of at least one respiratory controller agent;
    multiple dosages of at least one respiratory rescue agent in an aerosol delivery device;
    indicia for distinguishing said at least one controller agent and said at least one rescue agent;
    instructions for coordinating the use of said at least one controller agent and, said at least one rescue agent, said coordinating instructions including a fixed frequency of dosing of said at least one controller agent on a regular basis, a variable frequency of dosing of said at least one rescue agent where said at least one rescue agent is used when required for breakthrough of symptoms, and assessing the frequency of dosing of said at least one rescue agent relative to said frequency of dosing of said at least one controller agent; and
    a unifying container containing said at least one respiratory controller agent, said at least one respiratory rescue agent, said indicia, and said instructions.

2. The system of claim 1 wherein said coordinating instructions further include adjusting said fixed frequency of dosing of said at least one controller agent based on said frequency of dosing of said at least one rescue agent.

3. The system of claim 1 further comprising an actuation monitor configured to monitor the number of times said at least one rescue agent is used.

4. The system of claim 3 wherein said actuation monitor is a separate monitor adapted for use with said aerosol delivery device of said rescue agent.

5. The system of claim 3 wherein said actuation monitor is integrally connected to said aerosol delivery device of said rescue agent.

6. The system of claim 1 wherein said at least one controller agent is selected from the group consisting of inhaled corticosteroids, long-acting bronchodilators, and leukotriene modifiers.

7. The system of claim 1 wherein said at least one rescue medication is albuterol.

8. A therapeutic method that facilitates the assessment of need for controller medication in obstructive pulmonary disease, said method comprising:
    manufacturing a unifying container that contains multiple dosages of at least one respiratory controller agent, multiple dosages of at least one aerosol respiratory rescue agent, and indicia for distinguishing said at least one controller agent and said at least one rescue agent;

devising instructions for coordination the use of said at least one controller agent and said at least one rescue agent, said coordinating instructions including a fixed frequency of dosing of said at least one controller agent, a variable frequency of dosing of said at least one rescue agent where said at least one rescue agent is used when required for breakthrough of symptoms, and assessing the frequency of dosing of said at least one rescue agent relative to said frequency of dosing of said at least one controller agent; and incorporating said instructions within said unifying container.

9. The method of claim 8 wherein said instruction devising step further includes adjusting said fixed frequency of dosing of said at least one controller agent based on said frequency of dosing of said at least one rescue agent.

10. The method of claim 8 wherein said manufacturing step further includes providing an actuation monitor configured to monitor the number of times said at least one rescue agent is used.

11. A therapeutic method that facilitates the assessment of need for controller medication in obstructive pulmonary disease, said method comprising:

prescribing a prepackaged unifying container that contains multiple dosages of at least one respiratory controller agent, multiple dosages of at least one aerosol respiratory rescue agent, indicia for distinguishing between said controller agent and said rescue agent, and instructions for coordinating the use of said at least one controller agent and said rescue agent, said coordinating instructions including fixed frequency of dosing of said at least one controller agent on a regular basis, a variable frequency of dosing of said at least one rescue agent where said at least one rescue agent is used when required for breakthrough of symptoms, assessing said variable frequency of dosing of said at least one rescue agent relative to said fixed frequency of dosing of said at least one controller agent, and alerting a user to monitor over-dependence on said rescue medication;

reviewing the use of said at least one controller agent and said at least one rescue agent; and adjusting controller agent utilization in accord with utilization of said rescue medication.

12. The method of claim 11 wherein said prescribing step further includes providing an actuation monitor configured to monitor the number of times said at least one rescue agent is used.

13. A therapeutic method that facilitates the assessment of need for controller medication in obstructive pulmonary disease, said method comprising:

obtaining a prepackaged unifying container that contains multiple dosages of at least one respiratory controller agent, multiple dosages of at least one aerosol respiratory rescue agent, indicia for distinguishing said controller agent and said rescue agent, and instructions for using said at least one controller agent and said at least one rescue agent, said coordinating instructions including a fixed frequency of dosing of said at least one controller agent on a regular basis, a variable frequency of dosing of said at least one rescue agent where said at least one rescue agent is used when required for breakthrough of symptoms assessing said variable frequency of dosing of said at least one rescue agent relative to said fixed frequency of dosing of said at least one controller agent, and alerting a user to monitor over-dependence on said rescue medication; and adjusting said frequency of dosing of said at least one controller agent in accord with utilization of said rescue agent with the advice of a caregiver.

14. The method of claim 13 wherein said obtaining step further includes instructing the user that said frequency of dosing of said rescue agent is a determinant for adjusting said frequency of dosing of said controller agent.

15. The method of claim 13 wherein said obtaining step further includes obtaining an actuation monitor configured to monitor the number of times said at least one rescue agent is used.

16. A therapeutic method that facilitates the assessment of need for controller medication in obstructive pulmonary disease, said method comprising:

dispensing a unifying container that contains multiple dosages of at least one respiratory controller agent, multiple dosages of at least one aerosol respiratory rescue agent, indicia for distinguishing said controller agent and said rescue agent, and instructions for using said at least one controller agent and said at least one rescue agent, said instructions including a fixed frequency of dosing of said at least one controller agent on a regular basis, a variable frequency of dosing of said at least one rescue agent where said at least one rescue agent is used when required for breakthrough of symptoms, assessing said variable frequency of dosing of said at least one rescue agent relative to said fixed frequency of dosing of said at least one controller agent, and alerting a user to monitor over-dependence on said rescue agent.

17. The method of claim 16 wherein said instructions further includes adjusting said fixed frequency of dosing of said at least one controller agent based on said variable frequency of dosing of said at least one rescue agent.

18. The method of claim 16 wherein said dispensing step further includes dispensing an actuation monitor configured to monitor the number of times said at least one rescue agent is used.

19. A prepackaged therapeutic device for reducing medication error and side-effects in the use of combined controller and rescue treatments for obstructive respiratory disorders, said device comprising:

respiratory controller means for providing a long-term controller medication;

respiratory rescue means for providing a fast-acting rescue medication;

indicia means for distinguishing said controller means from said rescue means;

instruction means for coordinating the use of said controller means and said rescue means, said instruction means including a fixed frequency of dosing of said respiratory controller means, a variable frequency of dosing of said respiratory rescue means where said respiratory rescue means is used when required for breakthrough of symptoms, assessing said variable frequency of dosing of said respiratory rescue means relative to said fixed frequency of dosing of said respiratory controller means, and alerting a user to monitor over-dependence on said respiratory rescue means; and container means for unifying said controller means, said rescue means, said instruction means, and said indicia means.

20. The device of claim 19 further including actuation recording means for recording the number of times a user uses said respiratory rescue means.

21. The device of claim 20 wherein said actuation recording means is a separate monitor adapted for use with said rescue means.

22. The device of claim 20 wherein said actuation recording means is an actuation monitor integrally connected to said rescue means.

23. The device of claim 19 wherein said controller means includes at least a first controller medication and a second controller medication.

24. The device of claim 19 wherein said long-term controller medication is selected from the group consisting of inhaled corticosteroids, long-acting bronchodilators, and leukotriene modifiers.

25. The device of claim 19 wherein said fast-acting rescue medication is albuterol.

* * * * *